United States Patent
Kitajima et al.

(10) Patent No.: US 10,383,532 B2
(45) Date of Patent: Aug. 20, 2019

(54) METHOD AND APPARATUS FOR MEASURING HEART RATE

(71) Applicant: SAMSUNG ELECTRONICS CO., LTD., Suwon-si (KR)

(72) Inventors: Toshihiro Kitajima, Yokohama (JP); Edwardo Murakami, Yokohama (JP); Sang-on Choi, Suwon-si (KR)

(73) Assignee: SAMSUNG ELECTRONICS CO., LTD., Swuon-si (KR)

( * ) Notice: Subject to any disclaimer, the term of this patent is extended or adjusted under 35 U.S.C. 154(b) by 347 days.

(21) Appl. No.: 14/551,327

(22) Filed: Nov. 24, 2014

(65) Prior Publication Data
US 2015/0148687 A1   May 28, 2015

(30) Foreign Application Priority Data
Nov. 22, 2013 (JP) ................. 2013-241591

(51) Int. Cl.
| | |
|---|---|
| *A61B 5/024* | (2006.01) |
| *A61B 5/117* | (2016.01) |
| *A61B 5/00* | (2006.01) |
| *A61B 5/1171* | (2016.01) |
| *A61B 5/103* | (2006.01) |

(52) U.S. Cl.
CPC ........ *A61B 5/02427* (2013.01); *A61B 5/1032* (2013.01); *A61B 5/1176* (2013.01); *A61B 5/6898* (2013.01); *A61B 5/7203* (2013.01); *A61B 5/742* (2013.01); *A61B 5/7485* (2013.01)

(58) Field of Classification Search
CPC . A61B 5/02427; A61B 5/1032; A61B 5/1176; A61B 5/6898; A61B 5/7203; A61B 5/742; A61B 5/7485
See application file for complete search history.

(56) References Cited

U.S. PATENT DOCUMENTS

| | | |
|---|---|---|
| 2008/0200820 A1 | 8/2008 | Amitzur et al. |
| 2011/0251493 A1 | 10/2011 | Poh et al. |
| 2012/0283535 A1 | 11/2012 | Sarussi |

(Continued)

FOREIGN PATENT DOCUMENTS

| | | |
|---|---|---|
| EP | 2 438 849 A1 | 4/2012 |
| JP | 6-217946 A | 8/1994 |
| JP | 07-124126 | 5/1995 |

(Continued)

OTHER PUBLICATIONS

Xu et al. "Robust efficient estimation of heart rate pulse from video" Biomedical Optics Express. vol. 5, No. 4. 2014.*

(Continued)

*Primary Examiner* — Michael T Rozanski
(74) *Attorney, Agent, or Firm* — Sughrue Mion, PLLC

(57) ABSTRACT

Provided is a method of measuring a heart rate in an electronic device. The method includes obtaining a face image of a subject by using the electronic device; determining a target region within the obtained face image; analyzing color information within the determined target region; and determining a heart rate of the subject on the basis of the analyzed color information. The analyzing of color information is performed on the basis of a differential arithmetic operation between a first color component and a second color component within the target region.

19 Claims, 15 Drawing Sheets

(56) References Cited

U.S. PATENT DOCUMENTS

2014/0023236 A1   1/2014  Jeanne et al.
2014/0192177 A1*  7/2014  Bartula ................. G06T 7/0016
                                                          348/77

FOREIGN PATENT DOCUMENTS

| | | |
|---|---|---|
| JP | 2005-218507 A | 8/2005 |
| JP | 2006-516000 A | 6/2006 |
| JP | 2011-130996 A | 7/2011 |
| JP | 2012-519894 A | 8/2012 |
| JP | 2012-239661 A | 12/2012 |
| JP | 20140200390 A | 10/2014 |
| WO | 2012/093358 A1 | 7/2012 |
| WO | 2013/030739 A1 | 3/2013 |

OTHER PUBLICATIONS

Heisele et al. "A Component-based Framework for Face Detection and Identification" International Journal of Computer Vision. 2006.*
De Haan et al. "Robust Pulse Rate From Chrominance-Based rPPG" IEEE Transactions on Biomedical Engineering, vol. 60, No. 10, Oct. 2013; p. 2878-2886. (Date of Publication: Jun. 4, 2013).*
Ming-Zher Poh et al.; "Non-contact, automated cardiac pulse measurements using video imaging and blind source separation"; Optics Express; vol. 18; No. 10; May 10, 2010; pp. 10762-10774.
Communication dated Dec. 19, 2017, issued by the Japanese Patent Office in counterpart Japanese Application No. 2013-241591.
Communication dated Jul. 11, 2017 issued by the Japanese Patent Office in counterpart Japanese Application No. 2013-241591.

* cited by examiner

METHOD AND APPARATUS FOR MEASURING HEART RATE

RELATED APPLICATION

This application claims the benefit of Japanese Patent Application No. 2013-0241591, filed on Nov. 22, 2013, in the Japanese Patent Office, the disclosure of which is incorporated herein in its entirety by reference.

BACKGROUND

1. Field

One or more exemplary embodiments relate to a method and apparatus for measuring a heart rate, and more particularly, to a method of measuring a heart rate by analyzing a face image in a non-contact manner.

2. Description of the Related Art

A method of measuring a heart rate of a subject by analyzing an image obtained using an optical image sensor has been studied. For example, average values of red, green, and blue within a face region image are calculated, and are then processed by an independent component analysis (ICA), and thus a heart rate may be measured from a peak frequency obtained by a frequency analysis of one component waveform.

SUMMARY

One or more exemplary embodiments include a method and apparatus for measuring a heart rate.

Additional aspects will be set forth in part in the description which follows and, in part, will be apparent from the description, or may be learned by practice of the presented exemplary embodiments.

According to one or more exemplary embodiments, a method of measuring a heart rate in an electronic device includes obtaining a face image of a subject by using the electronic device; determining a target region within the obtained face image; analyzing color information within the determined target region; and determining a heart rate of the subject on the basis of the analyzed color information. The analyzing of color information is performed on the basis of a differential arithmetic operation between a first color component and a second color component within the target region.

The target region may be determined on the basis of a face organ of the subject.

The face organ of the subject may include eyes, a nose, and a mouth which are positioned in a face of the subject.

The first color component and the second color component may be a green color and a red color which are primary colors of an RGB color system.

The determining of a heart rate of the subject may include converting the differential signal into a frequency signal in a frequency domain, and determining a frequency corresponding to a peak of the converted frequency signal to be a heart rate of the subject.

The method may further include recognizing a face of the subject in an image region obtained by the electronic device.

The method may further include displaying information required to obtain the face image again when the determined heart rate of the subject is not in a range which is set in advance in the electronic device.

The method may further include obtaining an image comprising a face of the subject.

According to one or more exemplary embodiments, an apparatus for measuring a heart rate by using an electronic device includes a face recognizer for recognizing a face region in an obtained image; a face organ detector for detecting a face organ in the recognized face region; a target region setting unit for setting a target region on the basis of the detected face organ; a noise reducer for reducing a noise component on the basis of a differential arithmetic operation between a first color component and a second color component within the set target region; and a heart rate detector for determining a heart rate of the subject on the basis of a color component having a reduced noise component.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
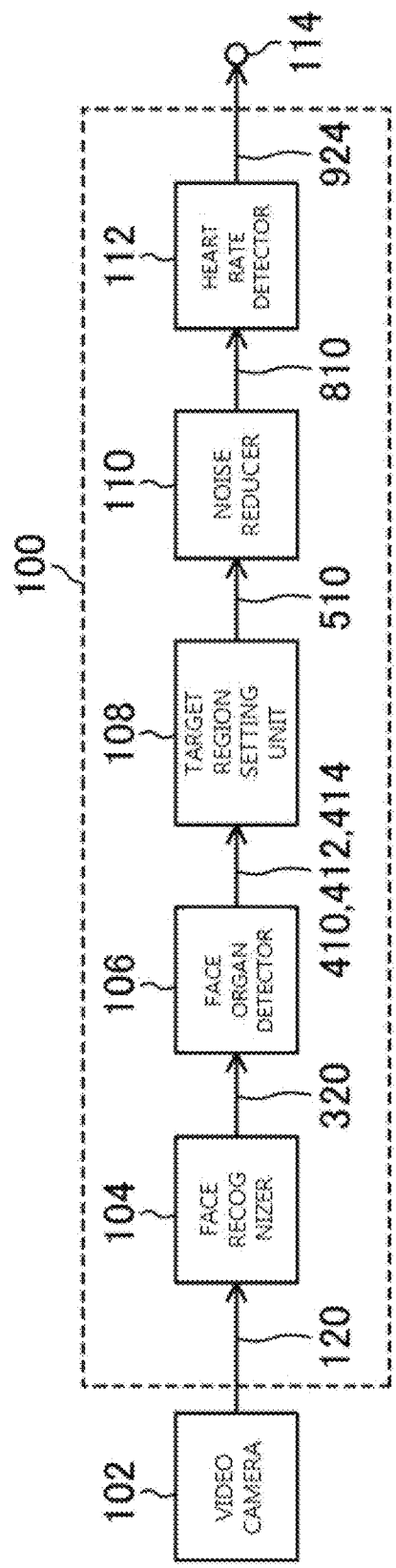
FIG. 1 shows a heart rate measurement system according to an exemplary embodiment.

Reference will now be made in detail to exemplary embodiments, examples of which are illustrated in the accompanying drawings, wherein like reference numerals refer to like elements throughout. In the drawings, the thicknesses of layers and regions are exaggerated for clarity.

In this regard, the present exemplary embodiments may have different forms and should not be construed as being limited to the descriptions set forth herein.

First, terms used to clarify a description of the exemplary embodiment will be briefly described.

A "subject" may be a human to be subjected to heart rate measurement. A user of a heart rate measurement system that measures a heart rate may be a subject. However, the subject of the exemplary embodiment is not limited to a human, and may be widely analyzed as a living organism with a measurable heart.

A "face organ" means a body organ located in a face. The face organ may be analyzed as a concept including parts of the body such as an eyebrow and hairs in addition to body organs such as an eye, a nose, a mouse, and an ear.

The movement of a face includes a change in the position of the face with respect to each of frames constituting a moving picture, a change in the direction of the face, a change in face expression, and the like. A change in a luminance value due to the movement of the face may be referred to as a body motion noise.

An RGB color system is a color space which is expressed by a red (R) component, a green (G) component, and a blue (B) component. In the present disclosure, an "R component", a "G component", and a "B component" mean a red component, a green component, and a blue component which are primary colors of the RGB color system.

An HSV color system is a color space which is expressed by hue, chroma, and brightness. In addition, a YUV color system is a color space which is expressed by a luminance signal Y and two color-difference signals.

The term "average" used herein includes a weighted average obtained by performing weighting and averaging and a simple average that does not require weighting.

Typically, a processor is a central processing unit (CPU), but is not limited thereto. The processor includes any hardware capable of executing programs according to various embodiments. In addition, the hardware may include a plurality of processors.

A memory that stores programs according to various embodiments may include not only a single memory but also a plurality of memories.

In the present disclosure, the term "or" used herein includes exclusive OR. For example, "P or Q" includes "P", "O", and "P and Q".

Hereinafter, a method of measuring a heart rate using a heart rate measurement system according to an exemplary embodiment will be described in detail with reference to FIGS. 1 to 12.

FIG. 1 shows a heart rate measurement system 100 according to an exemplary embodiment.

The heart rate measurement system 100 may be a portion of an electronic device such as a television or a mobile phone and means a device capable of receiving and processing an image (including a moving picture). As shown in FIG. 1, the heart rate measurement system 100 may receive moving picture data including a face of a subject from a video camera 102. At this time, the video camera 102 may be included in the heart rate measurement system 100, and may be a module provided separately from the heart rate measurement system 100. For example, the video camera 102 may be built in a television case or may be built in a mobile phone case.

In general, the video camera 102 may captures a moving picture by a complementary metal-oxide semiconductor (CMOS) image sensor and may output the captured moving picture. The video camera 102 may be a camera using a different type of image sensor such as a charge coupled device (CCD). The captured moving picture may be expressed by image frames which are arrayed in time series.

The resolution of a moving picture which is output by the video camera 102 is, for example, 1920*1080 pixels for full-HD), and a frame rate is 30 frames per second. However, the resolution is not limited thereto. The resolution may be lower resolution (for example, 640*480 pixels), or may be higher resolution. In addition, the frame rate is not limited to 30 frames per second, and may be other appropriate frame rates.

The heart rate measurement system 100 may measure a heart rate of a subject on the basis of the moving picture for the face of the subject and may output the measured heart rate to a display device 114. The display device 114 may be, for example, a liquid crystal display of a television or may be a liquid crystal display of a mobile phone. The display device 114 may be a displayer using a light-emitting diode (LED) for displaying a heart rate.

Figure 2:
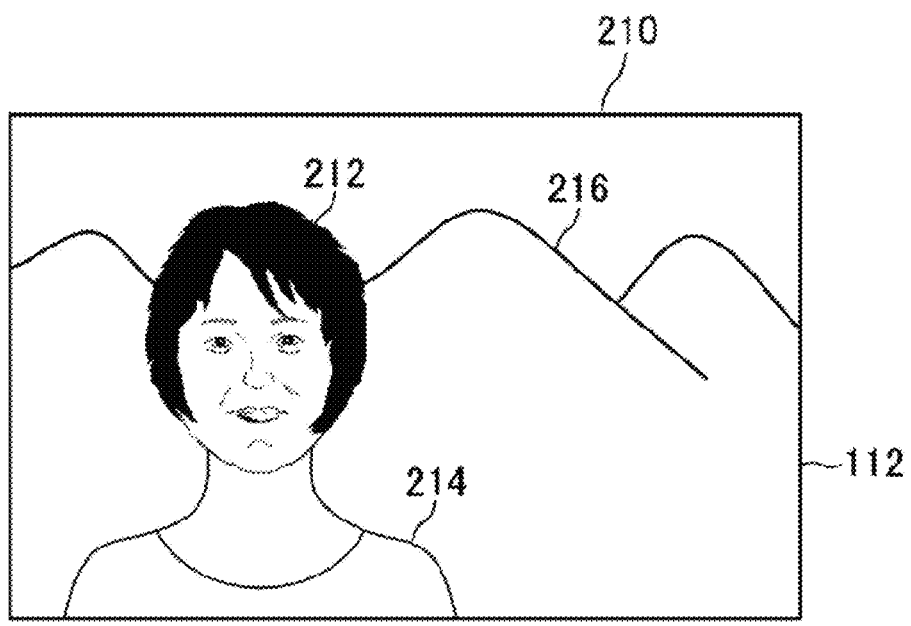
FIG. 2 shows a frame obtained from an optical image sensor according to an exemplary embodiment.

FIG. 2 shows a frame obtained using an optical image sensor according to the exemplary embodiment.

As illustrated in FIG. 2, a face recognizer 104 may receive a video signal 120 from the video camera 102. Typically, the video camera 102 is a digital video signal, and a moving picture may be expressed using three primary colors of the RGB color system. However, the video signal 120 is not limited thereto, and a moving picture may be expressed using three primary colors of an HSV color system or a YUV color system. When the video signal 120 does not include pixel data corresponding to colors used for a noise reducer 110 to be described later, a signal converter may convert the video signal 120 so as to include pixel data corresponding to colors used for the noise reducer 110. However, the signal converter may be located between the video camera 102 and the face recognizer 104, or may be included in the face recognizer 104.

As illustrated in FIG. 2, a frame 210, which is a full-HD moving picture captured by the video camera 102, may be 1920 pixels wide and 1080 pixels high. However, the exemplary embodiment is not limited thereto, and the resolution of a moving picture frame captured by the video camera 102 may be widely analyzed as resolution which is enough to obtain a target region to be described later.

Among moving pictures expressed by the video signal 120, one frame 210 may include a face 212 and a body 214 of a subject and objects 216 (foreground and background) except for the subject. The face recognizer 104 may identify the face 212 of the subject in the frame 210.

Figure 3:
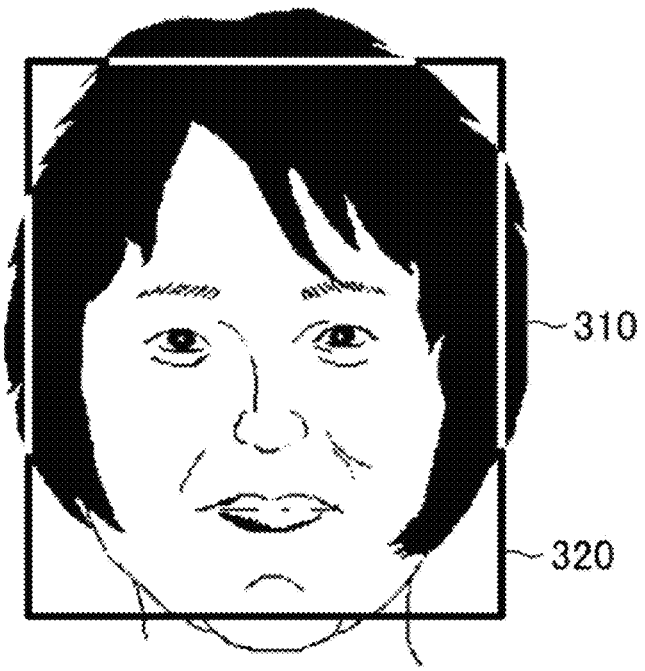
FIG. 3 shows a face region of a subject within a frame according to an exemplary embodiment.

FIG. 3 shows a face region of a face within a frame according to the exemplary embodiment.

As shown in FIG. 3, the face recognizer 104 may recognize a face 310 of a subject with respect to each frame of a moving picture indicated by the video signal 120. As a method of recognizing a face, an appropriate face recognition method of the related art may be used. When the face recognizer 104 determines that a face is present within a frame, the face recognizer 104 may determine that the face is a face 310 of a subject and may determine a face region 320 corresponding to the face 310.

Figure 4:
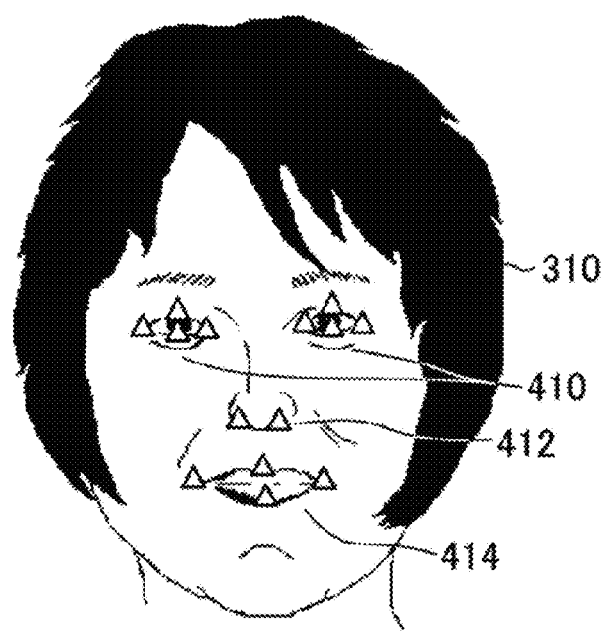
FIG. 4 shows a face organ of a subject according to an exemplary embodiment.

FIG. 4 shows face organs of the subject according to the exemplary embodiment.

As shown in FIG. 4, a face organ detector 106 may receive a signal indicating the face region 320 from the face recognizer 104 to thereby detect a face organ of a subject positioned within the face region 320. For example, the face organ is eyes 410, a nose 412, and a mouth 414, but is not limited thereto. The face organ may include various body parts positioned in the face. The face organ detector 106 may output data indicating the positions of the eyes 410, the nose 412, and the mouth 415 to a target region setting unit 108.

Figure 5:
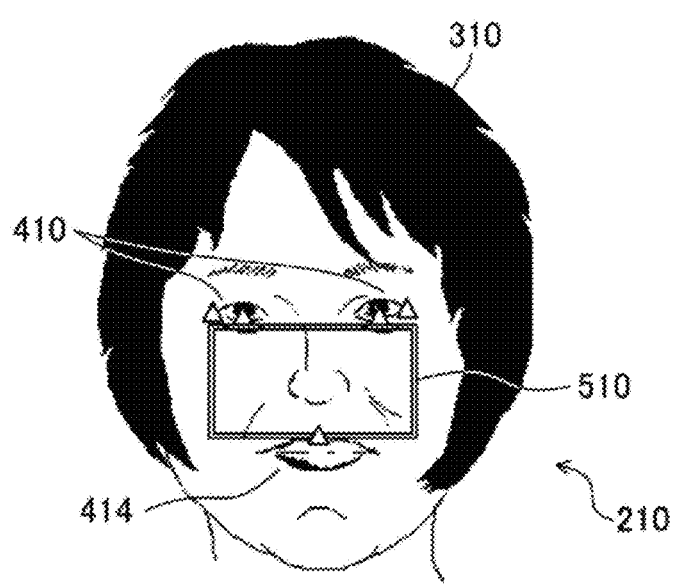
FIG. 5 shows a partial target region of a face of a subject according to an exemplary embodiment.

FIG. 5 shows a partial target region of the face of the subject according to the exemplary embodiment.

As shown in FIG. 5, the target region setting unit 108 may receive data indicating the positions of the eye 410, the nose 412, and the mouth 414 of the subject from the face organ detector 106. The target region setting unit 108 may set a target region 510, which is used to measure a heart rate, from the frame 210 on the basis of the position of the face organ of the subject. The target region setting unit 108 may set the target region 510 on the basis of the nose 412 in addition to the eyes 410 and the mouth 414. The target region 510 may be, for example, a region of 100 pixels wide and 100 pixels high, but is not limited thereto.

The target region 510 is a region of the face in which the amount of movement according to the expression of the face is relatively small, and thus is suitable for the measurement of a heart rate. In addition, the target region 510 is positioned in the center of the face 310 of the subject. Accordingly, even when the face 310 of the subject moves within the frame 210, there is an advantage in that the influence on the measurement of a heart rate is reduced. According to the current exemplary embodiment, the target region 510 may be a rectangular region which is surrounded by a horizontal straight line connecting the lower ends of the eyes 410, a horizontal straight line passing the upper end of the mouth 414, and a vertical straight line passing the outer corners of the eyes 410.

The target region setting unit 108 outputs pixel value data within the target region 510 to the noise reducer 110. Alternatively, the target region setting unit 108 may output data indicating the position of the target region 510 with respect to the frame 210 to the noise reducer 110. The noise reducer 110 may have access to a video memory that stores pixel data of the video signal 120 in order to average luminance values to be described later.

The noise reducer 110 may receive pixel value data of the target region 510 from the target region setting unit 108 and may output a signal 810 having reduced noise components in addition to heart beat components. In more detail, the noise reducer 110 may obtain a difference between a luminance signal indicating an average of luminance values of a pixel group of the target region 510 and a signal of a noise component, and may output the difference as a differential signal.

A pixel value of a heartbeat component may vary according to a heartbeat of a subject. The noise component having a varying pixel value may be generated due to the movement of a face of the subject or due to a change in the intensity of ambient light with which the face of the subject is illuminated. The noise component changes the luminance value of the pixel group of the target region 510, and thus may hinder the detection of a heart beat component. Accordingly, the noise component may be removed, or may be reduced when it is difficult to remove the noise component. In general, the noise component is constituted by a frequency component which is lower than that of the heart beat component. However, the frequency of the noise component may not be necessarily lower than that of the heart beat component, and may be equal to or higher than that of the heart beat component.

Figure 6:
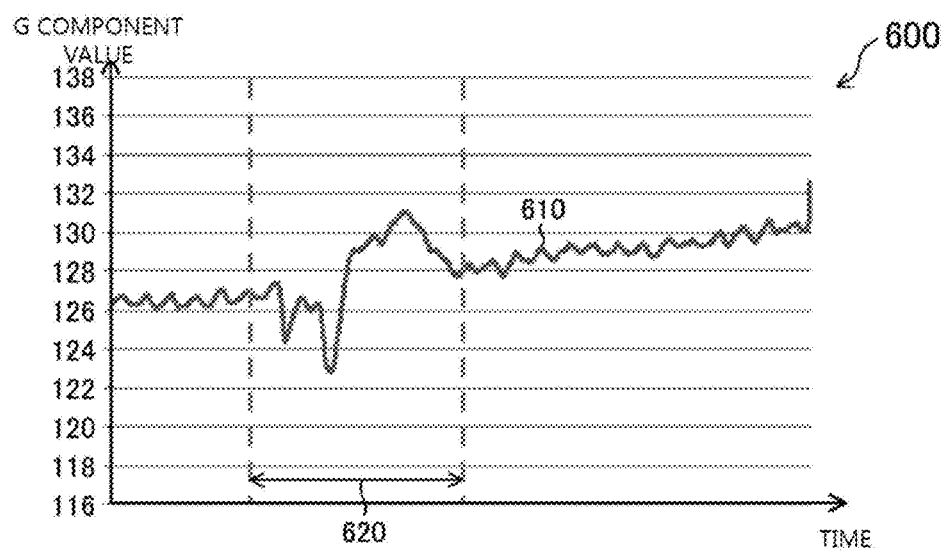
FIG. 6 is a graph showing time series data on an average value of green (G) components of a pixel group in a target region according to an exemplary embodiment.

FIG. 6 is a graph 600 showing time series data on an average value of green (G) components of a pixel group in a target region according to the exemplary embodiment.

As shown in FIG. 6, the noise reducer 110 may generate time series data 610 from the luminance value of the pixel group of the target region 510. For example, the time series data 610 may be an average value of G components sampled at time intervals of one-thirty seconds. This is because a frame rate of the video signal 120 is 30 frames per second. As described above, the frame rate of the present disclosure is not limited thereto, and may have any appropriate sampling rate. In section 620, the face 310 of the subject moves on the frame, and thus it may be understood that the time series data 610 also fluctuates significantly.

Figure 7:
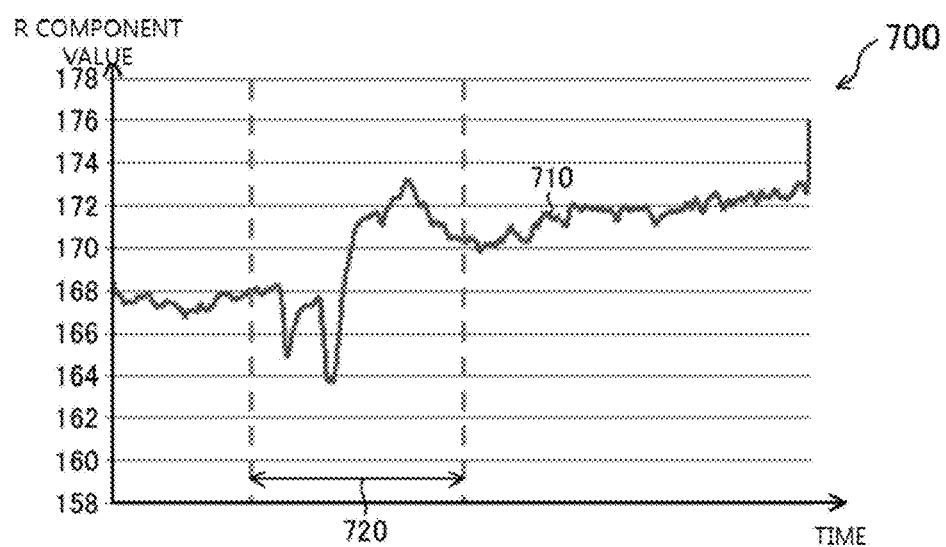
FIG. 7 is a graph showing time series data on an average value of red (R) components of a pixel group in a target region according to an exemplary embodiment.

FIG. 7 is a graph 700 showing time series data on an average value of red (R) components of a pixel group in a target region according to the exemplary embodiment.

The noise reducer 110 may generate time series data 710 from the luminance value of the pixel group of the target region 510. The graphs 600 and 700 are time series data which is obtained during the same time section of the video signal 120. Similarly to the section 620, the face 310 of the subject moves on the frame in the section 720, and thus it may be understood that the time series data 710 also fluctuates significantly.

Figure 8:
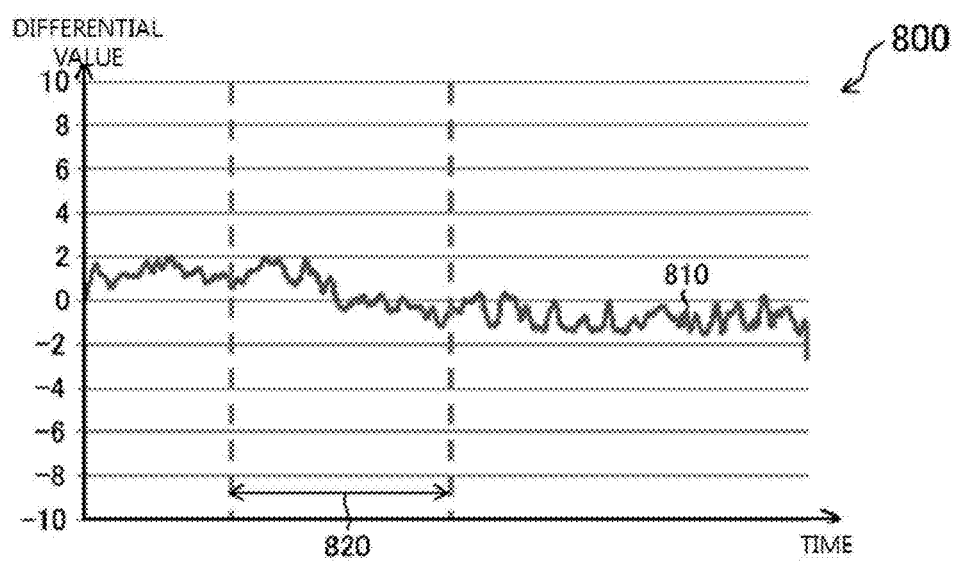
FIG. 8 is a graph showing time series data with respect to a signal obtained by differential operating time series data from another time series data according to an exemplary embodiment.

FIG. 8 is a graph showing time series data with respect to a signal obtained by differential operating time series data from another time series data according to the exemplary embodiment.

The noise reducer 110 may generate a differential signal obtained by subtracting the time series data 610 from the time series data 710, as time series data 810. The noise reducer 110 may output the generated time series data 810 to the heart rate detector 112. In spite of the face 310 of the subject which moves in the section 820, the time series data 810 does not fluctuate significantly. This is because the noise component due to the movement of the face of the subject is reduced by a differential operation between the R component and the G component. The differential operation may be reduced not only by a noise component due to the movement of the face but also by a change in the intensity of ambient light with which the face of the subject is illuminated.

Hereinafter, a difference between the R component and the G component among the RGB components will be described. When the amount of oxygenated hemoglobin flowing through blood vessels is increased by the heartbeat of the subject, the G component is absorbed into the face of the subject. Accordingly, among the RGB components of the video signal 120 which are reflected from the face, the G component includes the largest amount of heart beat components. On the other hand, the R component does not include a heartbeat component as large as the G component, and thus the noise component may be offset by obtaining a difference between the two components. In addition, it is not necessary to consider a sign of a differential signal in measuring a heart rate, and thus an absolute value of the difference may be used when obtaining the difference between the two components.

In the above-described example, the differential operation between the R component and the G component is used as a method of reducing a noise component. However, a differential operation between the B component and the G component may be used. Similarly to the differential operation between the R component and the G component, a differential operation between the B component and the G component has an effect of reducing a noise component.

Figure 9:
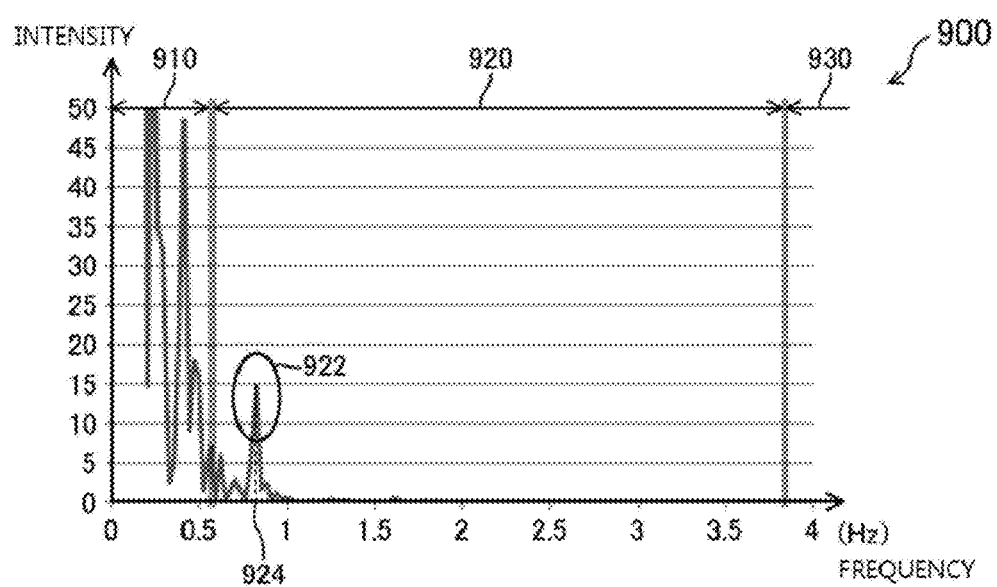
FIG. 9 shows a frequency spectrum in which time series data according to an exemplary embodiment is shown in a frequency domain.

FIG. 9 shows a frequency spectrum in which the time series data according to the exemplary embodiment is shown in a frequency domain.

The heart rate detector 112 may converts a normalized differential component (time series data 810) into a frequency component by fast Fourier transform (FFT). A frequency band may be divided into three range sections of a range 920 which may be taken as a heart rate, a frequency range 910 which is lower than the range 920, and a frequency range 930 which is higher than the range 920. The heart rate detector 112 may detect a peak value 922 within the range 920 and may output a frequency 924 corresponding to the peak value 922 to the display device 114 as a heart rate. As shown in FIG. 9, the frequency 924 of the peak value 922 may be 0.85 (Hz). In this case, a heart rate (HR) may be 0.85*60=51 (beat per minute; bpm).

As described above, the noise reducer 110 may reduce a noise component by a differential operation between the R component and the G component.

In order to detect the peak frequency 924, a point having the largest y coordinate value among coordinates on a plane may be regarded as a peak. The heart rate detector 112 may use linear fitting or curved fitting in order to detect a peak frequency with a higher level of accuracy. The fitting is a method of obtaining an x coordinate corresponding to a peak value from three points on the plane of (x−1, y), (x, y), and (x+1, y).

As an example of the linear fitting, a method according to the following expression may be used.

When SAD(x+1, y)<SAD(x−1, y), the following Expression 1 is obtained.

$$xsub = \frac{SAD(x+1, y) - SAD(x-1, y)}{2SAD(x, y) - SAD(x-1, y)} \quad (1)$$

When SAD(x+1, y)<SAD(x−1, y), the following Expression 2 is obtained.

$$xsub = \frac{SAD(x+1, y) - SAD(x-1, y)}{2SAD(x, y) - SAD(x+1, y)} \quad (2)$$

wherein, SAD denotes the sum of absolute differences) and xsub denotes a peak frequency.

As an example of the curved fitting, a parabolic fitting method according to the following expression may be used. The parabolic fitting method is as expressed by the following Expression 3.

$$xsub = \frac{SAD(x-1, y) - SAD(x+1, y)}{2SAD(x-1, y) - 4SAD(x, y) + 2SAD(x+1, y)} \quad (3)$$

When SAD(x+1, y)≥SAD(x−1, y), the following Expression 2 is obtained.

As shown in Expression 1 to Expression 3, when the linear fitting or the curved fitting is used to obtain the peak value, there is an effect of improving resolution at the time of determining a peak frequency.

As an alternative method of the above-mentioned differential operation, the noise reducer 110 may reduce a noise component by a differential operation from a moving average. Hereinafter, a method of reducing noise by a moving average will be described.

Figure 10:
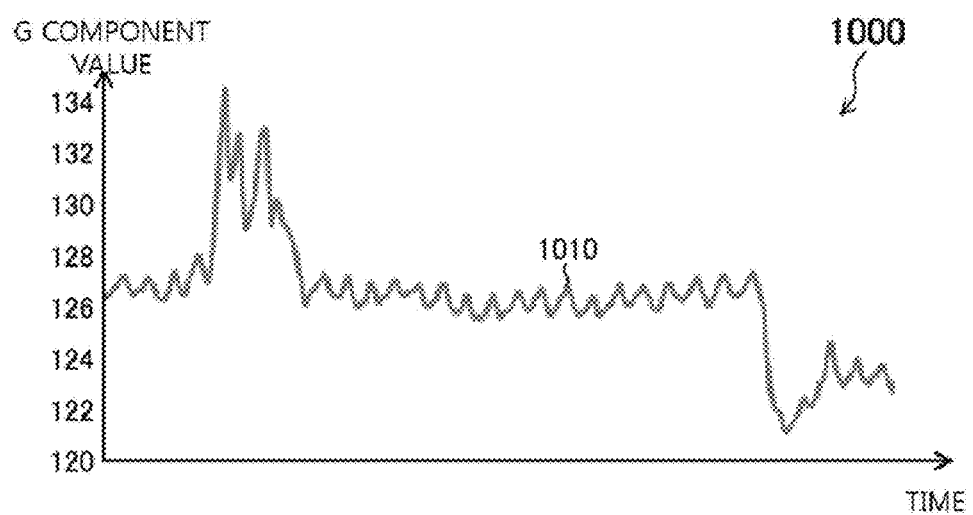
FIG. 10 is a graph showing time series data on an average value of green (G) components of a pixel group in a target region according to an exemplary embodiment.

FIG. 10 is a graph showing time series data on an average value of green (G) components of the pixel group in the target region according to the exemplary embodiment.

The noise reducer 110 may generate time series data 1010 from the luminance value of the pixel group of the target region 510.

Figure 11:
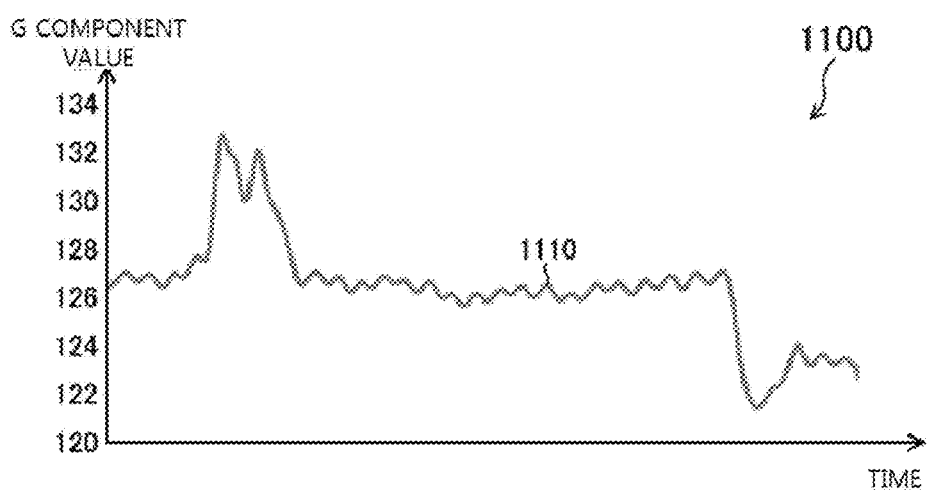
FIG. 11 is a graph showing time series data on results obtained by performing a moving average operation on time series data according to an exemplary embodiment.

FIG. 11 is a graph showing time series data on results obtained by performing a moving average operation on the time series data according to the exemplary embodiment.

The noise reducer 110 may generate time series data 1110 from the time series data 1010. The time series data 1110 may be obtained by repeatedly performing a moving average operation using continuous five sampling points on the time series data 1010 twenty times.

Figure 12:
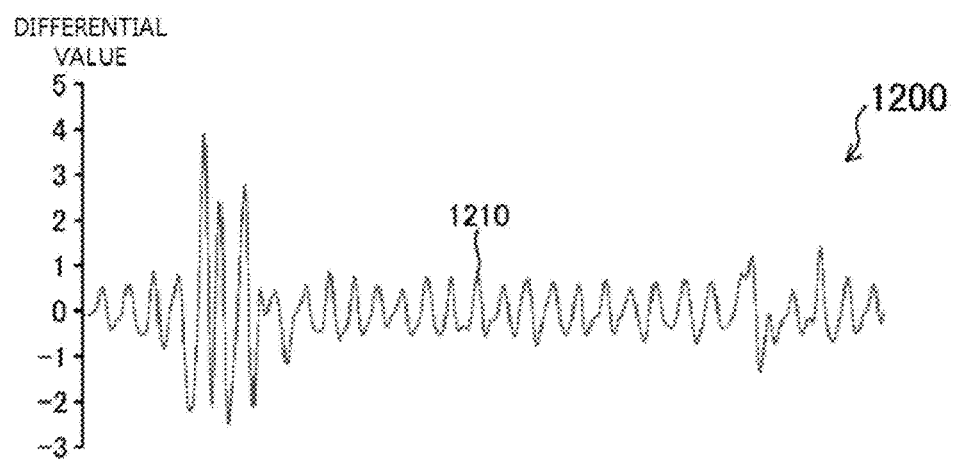
FIG. 12 is a graph showing time series data with respect to a signal obtained by differential operating time series data from another time series data according to an exemplary embodiment.

FIG. 12 is a graph showing time series data with respect to a signal obtained by differential operating time series data from another time series data according to the exemplary embodiment.

The noise reducer 110 may output a differential signal obtained by subtracting the time series data 1110 from the time series data 1010, as time series data 1210. The time series data 1210 is data corresponding to the time series data 810.

Figure 13:
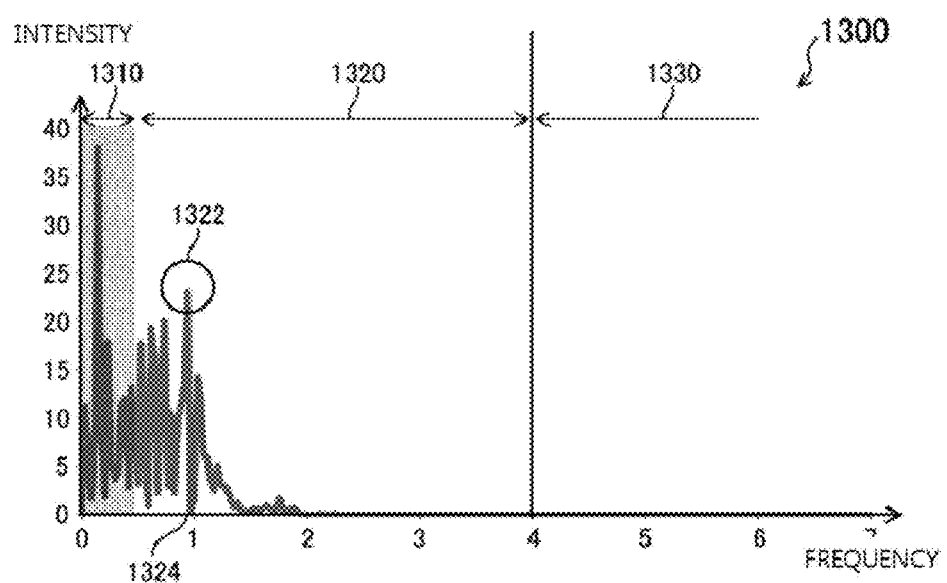
FIG. 13 shows a frequency spectrum in which time series data according to an exemplary embodiment is shown in a frequency domain.

FIG. 13 shows a frequency spectrum in which the time series data according to the exemplary embodiment is shown in a frequency domain.

Even when a moving average is used, the heart rate detector 112 may operate as described in FIG. 9. That is, the heart rate detector 112 converts a normalized differential component (time series data 1210) into a frequency component by fast Fourier transform (FFT). A frequency band may be divided into three ranges of a range 1320 which may be taken as a heart rate, a frequency range 1310 which is lower than the range 1320, and a frequency range 1330 which is higher than the range 1320. The heart rate detector 112 may detect a peak value 1322 within the range 13200 and may output a frequency 1324 in the peak value 1322 to the display device 114 as a heart rate.

As described above, when a differential operation between time series data and time series data in which a moving average is taken is performed, and thus even when a frequency component of light with which the face of the subject is irradiated is changed, there is an effect of reducing the influence of the change in the frequency component.

Figure 14:
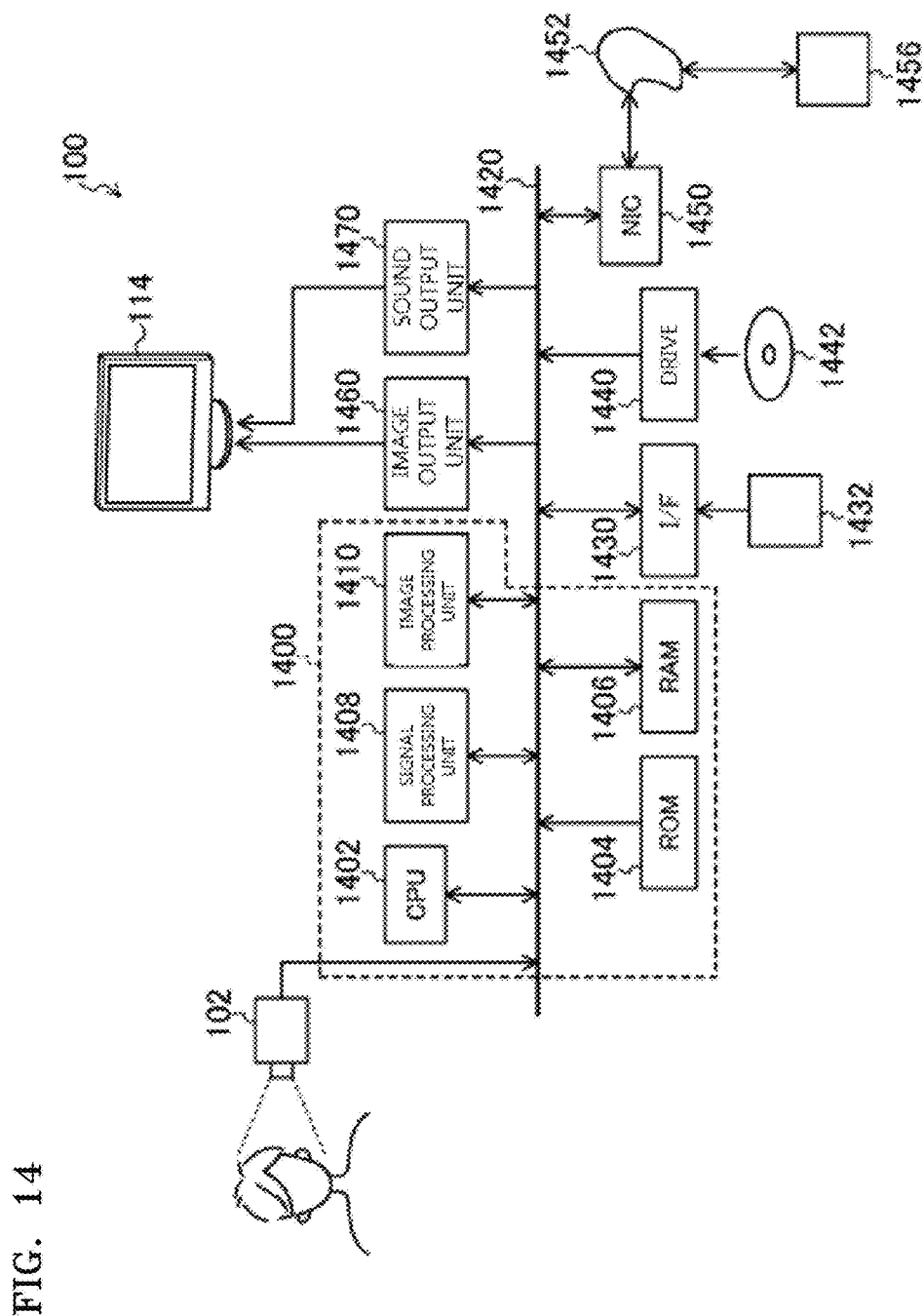
FIG. 14 is a block diagram showing the configuration of a device according to an exemplary embodiment.

FIG. 14 is a block diagram showing the configuration of a device according to the exemplary embodiment.

As shown in FIG. 14, the device may be an electronic device such as a television or a mobile phone, or may be a portion of the electronic device. The heart rate measurement system 100 may include a program execution unit 1400. The video camera 102, the display device 114, and the like may be coupled to the heart rate measurement system 100. The video camera 102 and the display device 114 may be positioned within the heart rate measurement system 100.

The program execution unit 1400 may be constituted by a CPU 1402, a ROM 1404, a RAM 1406, a signal processing unit 1408, and an image processing unit 1410. The program execution unit 1400 executes various operations described in the present disclosure by the CPU 1402, and realizes configurations corresponding to the operations. The program execution unit 1400 may realize the configurations shown in FIG. 1. The program execution unit 1400 may have various other configurations required to execute a program. In contrast, some of the configurations may be omitted.

The CPU 1402 may be connected to the components of the heart rate measurement system 100 through a bus 1420 to thereby control the whole operation by exchanging a control signal and data. The CPU 1402 may realize a desired operation by executing an element group constituting a program stored in the RAM 1406. The CPU 1402 may realize the configurations shown in FIG. 1.

The CPU 1402 may perform an arithmetic operation such as addition, subtraction, multiplication, and division, a logical operation such as OR, AND, and logical NOT, and a bit operation such as bitwise OR, bitwise AND, bit invert, bit shift, and bit rotation. The CPU 1402 may be configured to be capable of performing a saturation operation such as addition, subtraction, multiplication, and division for multimedia processing, and a vector operation such as a trigonometric function at high speed. The CPU 1402 may include a coprocessor in order to perform an operation at high speed.

The ROM 1404 may store an initial program loader (IPL) which is executed immediately after power is supplied. The CPU 1402 may read a program stored in the ROM 1404 by executing the IPL. The CPU 1402 causes the RAM 1406 to store the read program to thereby perform processing required to execute the program. The ROM 1404 may store a program of an operating system (OS) and various pieces of data which are required to control the heart rate measurement system 100.

The RAM 1406 may temporarily store data or a program. The RAM 1406 may store a program read from the ROM 1404 and a recording medium 1442, data associated with the program, data related to communication, and the like. The CPU 1402 may provide a variable region in the RAM 1406 and may directly perform an operation on a value stored in the variable region. First, the CPU 1402 may store a value stored in the RAM 1406 in a register, may perform an operation on the register, and may transmit a result of the operation to a memory.

The interface 1430 may connect data related to a user's operation which is detected by a controller 1432 to the bus 1420 and may transmit the data to the CPU 1402 and the like. The signal processing unit 1408 and the image processing unit 1410 may be connected to the CPU 1402 through the bus 1420. The CPU 1402 may analyze a command from a program and may process and control various pieces of data. For example, the CPU 1402 may instruct the signal processing unit 1408 to process image data. The signal processing unit 1408 may perform various calculations such as segmentation of pixels of a target region from an image signal and calculation of an average of pixel values of a target region, and may generate image and sound data.

The recording medium 1442 refers a computer readable recording medium. The recording medium 1442 may store a program according to the present disclosure and data associated with the program. A drive 1440 may read the program and the data associated with the program from the recording medium 1442 under the control of the CPU 1402. The CPU 1402 may connect the read program and data to the bus 1420 and may transmit the program and data to the RAM 1406 to thereby cause the RAM 1406 to temporarily store the program and data.

The image output unit 1460 may perform image processing of displaying a measured heart rate on the display device 114.

A sound output unit 1470 may include a digital analog converter (DAC). The sound output unit 1470 may output a sound corresponding to the measured heart rate. For example, the display device 114 may be a liquid crystal display.

The program execution unit 1400 may further include other hardware or software elements in addition to the above-mentioned components. For example, the program execution unit 1400 may increase a calculation speed by performing parallel processing using a plurality of CPUs instead of using a single CPU 1402. In contrast, the program execution unit 1400 may not include some of the above-mentioned components. The image output unit 1460 may include a digital analog converter and a frame memory. The frame memory may store image data which is processed by the image processing unit 1410.

A network interface 1450 may be used to communicate with an external device 1456 through a network 1452. For example, data indicating a heart rate of a subject may be transmitted to the external device 1456. Thus, the heart rate of the subject may be directly transmitted to medical personnel at remote locations without interposing the measurement of the heart beat of the subject. In contrast, the heart rate measurement system 100 executes a program that measures a heart beat without having access to the network 1452 so that the subject may recognize his or her heart rate by the display device 114.

The program according to the present disclosure may be loaded to the RAM 1406 from the ROM 1404, but is not limited thereto. The entirety or a portion of the program according to the present disclosure may be connected to the network 1452 and may be located from a computer at a remote location. The entirety or a portion of data related to the program according to the present disclosure may be connected to the network and may be located from a computer (or a server) at a remote location.

Figure 15:
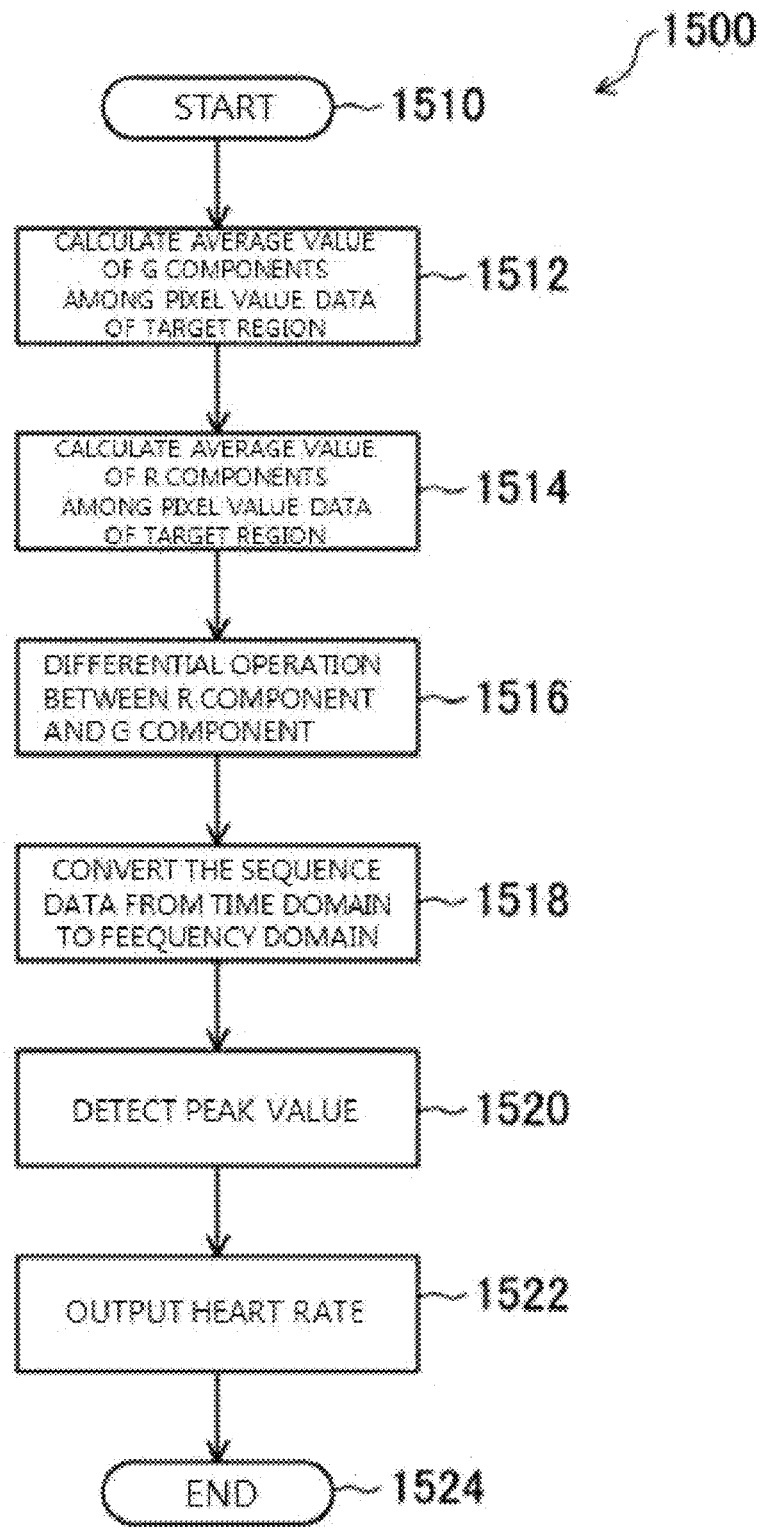
FIG. 15 is a flowchart showing an operation procedure of a noise reducer according to an exemplary embodiment.

FIG. 15 is a flowchart showing an operation procedure of a noise reducer according to the exemplary embodiment.

As shown in FIG. 15, a program shown by a flowchart 1500 may be loaded to the RAM 1406 from the ROM 1404 or the recording medium 1442 and may be temporarily stored. Thereafter, the program may be executed by the CPU 1402, and data indicating a heart rate may be output through the bus 1420. The output data may be displayed on the display device 114 and may be recognized by a subject as a user.

In FIGS. 6 to 9, a program for executing a differential arithmetic operation between the R component and the G component has been described. However, the present disclosure is not limited thereto, and various other embodiments may be given. For example, it is also possible to perform a differential arithmetic operation between the G component described in FIGS. 10 to 13 and a G component subjected to a moving average operation.

In step 1510, a program may be started by a trigger. For example, a subject may start the program by operating the controller 1432, such as a switch, of the heart rate measurement system 100.

In step 1512, an average value of the G components in the pixel value data of the target region 510 may be obtained. For example, when the target region 510 is a region of 100 pixels wide and 100 pixels high, an average value of the G components of a total of 10000 pixels may be obtained. The target region 510 is provided with respect to each frame of the video signal 120, and thus the time series data 610 which is an average value of the G components may be a variable varying over time.

In step 1514, an average value of the R components in the pixel value data of the target region 510 may be obtained. For example, when the target region 510 is a region of 100 pixels wide and 100 pixels high, an average value of the R components of a total of 10000 pixels may be obtained. The target region 510 is set with respect to each frame of the video signal 120, and thus the time series data 610 which is an average value of the R components may be a variable varying over time.

In step 1516, the time series data 810 which is a differential signal obtained by subtracting the time series data 610 from the time series data 710 may be obtained. The time series data 610 and the time series data 710 may be obtained over a long period of time to the extent that a frequency component (substantially, intervals of 1 Hz) based on a heart rate may be extracted later. The time series data 610 and time series data 710 may be based on the video signal 120 at intervals of several seconds.

In step 1518, a frequency spectrum 900 may be obtained by converting the time series data 810 from a time region to a frequency domain. For example, this conversion may be performed by fast Fourier transform (FFT).

In step 1520, a peak value corresponding to a heart rate which is present in a middle region, except for noise components which may be present in low and high regions in the frequency spectrum, may be detected.

In step 1522, a heart rate may be obtained on the basis of a frequency of the detected peak value. The heart rate may be transformed to an appropriate format and may be output to the display device 114.

In step 1524, the heart rate measurement system may terminate the program. If necessary, the control of the program may be returned from step 1524 to step 1510 to repeatedly measure a heart rate. In addition, when a heart rate in an appropriate range is not measured in step 1522, a user may be notified of the gist of a measurement error and the control of the program may be returned to step 1510 to thereby perform the measurement again.

A series of processes shown in the flowchart 1500 are not necessarily performed in the order shown in the flowchart. The processes may be simultaneously performed, or pipeline processing of the processes may be performed. All the processes of the program shown in the flowchart 1500 may not be necessarily performed by a combination of hardware and software, and may be realized only by hardware.

Similarly to the noise reducer 110 realized by a combination of hardware and software, the other components of the heart rate measurement system 100 may be realized by a combination of hardware and software. In addition, operations of the other components of the heart rate measurement system 100 may not be necessarily performed by a combination of hardware and software, and may be realized only by hardware. For example, the entirety or a portion of the heart rate measurement system 100 may be realized by using an application specific integrated circuit (ASIC).

As another exemplary embodiment of the method of measuring a heart rate which is described in the present disclosure, a G component and (R component+B component)/2 are obtained in step 1512 and step 1514, respectively. Then, in step 1516, a differential arithmetic operation may be performed. In addition to a noise component due to the movement of a subject, a noise component due to ambient light may be easily reduced by averaging the R component and the B component.

As another exemplary embodiment of the method of measuring a heart rate which is described in the present disclosure, two components in primary colors of an RGB color system, an HSV color system, or a YUV color system are obtained in step 1512 and step 1514, respectively. Then, in step 1516, a differential arithmetic operation may be performed.

As another exemplary embodiment of the method of measuring a heart rate which is described in the present disclosure, a subject is irradiated with light of in a near-infrared region, and a component of reflected light and a component obtained by performing a moving average operation on the component of reflected light are obtained in step 1512 and step 1514, respectively. Then, in step 1516, a differential arithmetic operation may be performed. Thus, there is an advantage in that the influence of ambient light is reduced. As another method, a subject may be irradiated with light in a near-infrared region or blue light which is a primary color of an RGB color system.

According to the above-described various embodiments, there is an advantage in that a heart rate may be accurately detected even when a noise component (in particular, a noise component due to the movement of a face) is present at a point in time when measurement is started, as compared with an independent component analysis.

Some of the above-mentioned various element groups of hardware and software may be omitted in a range understandable by one of ordinary skill in the art. In contrast, additional elements may be used. Some of the element groups of hardware and software may be realized by being grouped into a single element. In contrast, one of the element groups of hardware and software may be realized as a plurality of different element groups.

The exemplary embodiments of the present invention can be written as computer programs and can be implemented in general-use digital computers that execute the programs using a computer readable recording medium. Examples of the computer readable recording medium include magnetic storage media (e.g., ROM, floppy disks, hard disks, etc.), optical recording media (e.g., CD-ROMs, or DVDs), and storage media.

While this invention has been particularly shown and described with reference to preferred embodiments thereof, it will be understood by those of ordinary skill in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of measuring a heart rate of a subject in an electronic device, the method comprising:

obtaining, by at least one processor of the electronic device, a face image of the subject by using the electronic device;

performing, by the at least one processor, a differential arithmetic operation between a green color component and a red color component within the face image, wherein the performing the differential arithmetic operation comprises obtaining a differential signal as a difference between a first moving average of first pixel values of the green color component and a second moving average of second pixel values of the red color component;

converting, by the at least one processor, the differential signal into a frequency signal in a frequency domain; and determining, by the at least one processor, a heart rate of the subject based on the frequency signal, wherein the first pixel values of the green color component are obtained as a first time series, the second pixel values of the red color component are obtained as a second time series, the first moving average is determined based on the first pixel values which are successive in a first section in the first time series, and the second moving average is determined based on the second pixel values which are successive in a second section in the second time series.

2. The method of claim 1, wherein the determining the heart rate of the subject comprises:

determining a frequency corresponding to a peak of the frequency signal to be the heart rate of the subject.

3. The method of claim 1, further comprising recognizing, by the at least one processor, a face of the subject in an image region obtained by the electronic device.

4. The method of claim 1, further comprising displaying on a display a message when the heart rate of the subject is not in a range which is set in advance in the electronic device.

5. The method of claim 4, further comprising obtaining, by the at least one processor, the face image of the subject based on a user interaction to the displayed message.

6. The method of claim 1, wherein the first section is a certain time period in the first time series, and the second section is a certain time period in the second time series.

7. The method of claim 1, wherein the second section is a same time period as the first section.

8. The method of claim 1, wherein the face image includes a target region determined based on a face organ of the subject, and the differential arithmetic operation is performed based on the target region within the face image.

9. The method of claim 1, wherein the obtaining the face image comprises obtaining the face image of the subject based on an input of the subject operating an input device.

10. The method of claim 9, wherein the obtaining the face image further comprises determining that a face, which is present in the face image, is a face of the subject who uses the electronic device.

11. An apparatus for measuring a heart rate of a subject, the apparatus comprising:

at least one processor configured:

to obtain a face image of the subject, to perform a differential arithmetic operation between a green color component and a red color component within the face image by obtaining a differential signal as a difference between a first moving average of first pixel values of the green color component and a second moving average of second pixel values of the red color component, to convert the differential signal into a frequency signal in a frequency domain, and to determine a heart rate of the subject based on the frequency signal, wherein the first pixel values of the green color component are obtained as a first time series, the second pixel values of the red color component are obtained as a second time series, the first moving average is determined based on the first pixel values which are successive in a first section in the first time series, and the second moving average is determined based on the second pixel values which are successive in a second section in the second time series.

12. The apparatus of claim 11, wherein the at least one processor is further configured to determine a frequency corresponding to a peak of the frequency signal to be the heart rate of the subject.

13. The apparatus of claim 11, wherein the at least one processor is further configured to control a display to display a message when the heart rate of the subject is not in a range which is set in advance in the apparatus.

14. The apparatus of claim 13, wherein the at least one processor is further configured to obtain the face image of the subject based on a user interaction to the displayed message.

15. The apparatus of claim 11, wherein the first section is a certain time period in the first time series, and the second section is a certain time period in the second time series.

16. The apparatus of claim 11, wherein the second section is a same time period as the first section.

17. The apparatus of claim 11, wherein the face image includes a target region determined based on a face organ of the subject, and the differential arithmetic operation is performed based on the target region within the face image.

18. An apparatus for measuring a heart rate of a subject, the apparatus comprising:

at least one processor configured:

to obtain a face image of the subject, to perform a differential arithmetic operation between a first color component and a second color component within the face image by obtaining a differential signal as a difference between a first moving average of first pixel values of the first color component and a second moving average of second pixel values of the second color component, to convert the differential signal into a frequency signal, and to determine a frequency corresponding to a peak of the frequency signal to correspond to a heart rate of the subject, wherein a color of the first color component is different from a color of the second color component of RGB primary colors, the first pixel values of the first color component are obtained as a first time series, the second pixel values of the second color component are obtained as a second time series, the first moving average is determined based on the first pixel values which are successive in a first section in the first time series, and the second moving average is determined based on the second pixel values which are successive in a second section in the second time series.

19. The apparatus of claim 18, wherein the first color component is a G component and the second color component is a color component corresponding to an average value between an R component and a B component, of the RGB primary colors.

* * * * *